United States Patent [19]
Nakatsu

[11] Patent Number: 5,202,355
[45] Date of Patent: Apr. 13, 1993

[54] METHOD OF INHIBITING ALDOSE REDUCTASE IN DIABETIC HOSTS USING PHENOL DERIVATIVES

[75] Inventor: Tetsuo Nakatsu, Walnut Creek, Calif.

[73] Assignees: Takasago Institute for Interdisciplinary Science Inc., Walnut Creek, Calif.; Takasago International Corporation, Tokyo, Japan

[21] Appl. No.: 713,883

[22] Filed: Jun. 12, 1991

[51] Int. Cl.$^5$ ...................... A01N 37/10; A01N 31/08
[52] U.S. Cl. ................................... 514/568; 514/731; 514/866
[58] Field of Search ........................ 514/731, 866, 568

[56] References Cited

U.S. PATENT DOCUMENTS 4,185,116 1/1980 Barnish ............................... 424/319
4,423,075 12/1983 Dvornik ............................. 424/317

FOREIGN PATENT DOCUMENTS 6434913 2/1989 Japan.

OTHER PUBLICATIONS

Yasuda et al "Effect of . . . " *Diabetes* vol. 38; 832–838, Jul. 1989.
Itokawa et al "A Quantitative . . . " Chem. Abs. 111:166773q Nov. 6, 1989.
I. Kubo, et al., "Mulluscicides from the Cashew *Anacardium occidentale* and Their Large-Scale Isolation," J. Agric. Food Chem. 1986, 34, 970-973.
I. Kubo, et al., "Prostaglandin Synthetase Inhibitors from the African Medicinal Plant *Ozoroa mucronate*," Chem. Letters, 1987, 1101.

*Primary Examiner*—Frederick E. Waddell
*Assistant Examiner*—Gregory Hook
*Attorney, Agent, or Firm*—Spensley Horn Jubas & Lubitz

[57] ABSTRACT

The use of alkyl or alkenyl phenols or pharmaceutical acceptable salts thereof as aldose reductase inhibitors, and hence, as an agent for preventing or alleviating chronic diabetic complications.

2 Claims, No Drawings

METHOD OF INHIBITING ALDOSE REDUCTASE IN DIABETIC HOSTS USING PHENOL DERIVATIVES

BACKGROUND OF THE INVENTION

1. Field of the Invention

This invention relates to the use of alkyl or alkenyl phenols or their pharmaceutically acceptable base salts as aldose reductase inhibitors. More particularly, the invention relates to a method of ameliorating chronic complications arising in a galactosemic or diabetic host by administering to the host a therapeutically effective amount of the foregoing alkyl or alkenyl phenols or their pharmaceutically acceptable base salts as well as to compositions containing the same.

2. Related Art

Aldose reductase, an enzyme in the sorbitol pathway of glucose metabolism, catalyzes the reduction of various aldoses (such as glucose and galactose) to the corresponding polyols (such as sorbitol and glactitol).

In the lens of a galactosemic or diabetic host, the formation of excess sugar polyols followed by the osmotic accumulation of water leads to cataract formation [J. H. Kinoshita et al., Invest. Opthalmod., 13, 713 (1974)]. Thus, as the polyols accumulate to levels high enough to cause hypertonicity, lens fiber swells. This osmotic swelling triggers an electrolyte imbalance in the lens with loss in K+ and gain in Na+, accompanied by massive influx of water, which eventually results in lenticular opacity. The lenticular opacity is caused by the microaggregation or precipitation of the normally translucent lenticular proteins. This sequence of events is believed to be the mechanism of cataract formation in a galactosemic or diabetic host.

Alrestatin [AY-22, 284; 1,3-dioxo-1H-benz (de) isoquinoline-2(3H)-acetic acid] has heretofore been reported to successfully prevent galactosemic cataract formation in experimental rats by inhibiting aldose reductase, and therefore, by blocking the sugar polyol accumulations [D. Dvornik, et al., Science, 182, 1146 (1973)].

U.S. Pat. No. 4,348,526 to R. Sarges discloses another aldose reductase inhibitor known as sorbinil (d-6-fluoro-spiro [chroman-4,4'-imidazolidine]-2',5'-dione), which is one of the most potent inhibitors heretofore investigated. Sorbinil is reported to inhibit calf lens aldose reductase at the $IC_{50}$ concentration of $\sim 5 \times 10^{-7}$M.

In the peripheral nerve of a diabetic host, the accumulation of sugar polyols causes a slowing of conduction in nerve fiber. It is this decreased nerve conduction velocity in both sensory and motor nerves which characterizes diabetic neuropathy. It has been demonstrated that alrestatin and sorbinil improve motor nerve conduction velocity (MNCV) in both short and long-term streptozotocin induced diabetes in rats [K. H. Gabbay, Advances in Metabolic Disorders, Suppl. 2, New York, Academic Press, 1973, p. 417; D. R. Tomlinson et al., Diabetes, 33, 470 (1984)].

These aldose reductase inhibitors prevent or reduce unwanted accumulations of galactitol in the lens of galactosemic hosts and of sorbitol in the lens, peripheral nervous cord and kidney of diabetic hosts. Although both alrestatin and sorbinil originally showed promise in effectively controlling diabetic complications such as diabetic cataracts, neuropathy, and retinopathy, etc., in humans, they were found to have significant drawbacks. For example, no improvement was observed with alrestatin administered to diabetic patients suffering from peripheral nerve deterioration [K. H. Gabbay, et al., Metabolism, 28, 471 (1979)]. Furthermore, no beneficial effect was observed with sorbinol in a similar study [I. G. Lewin, et al., Diabetologia, 26, 445 (1984)]. Accordingly, a search continues to find improved inhibitors of aldose reductase which would be therapeutically useful in the treatment of diabetes-associated chronic complications.

SUMMARY OF THE INVENTION

It has now been discovered that certain naturally occurring alkyl or alkenyl phenols or pharmaceutically acceptable base salts thereof effectively inhibit the activity of aldose reductase.

In accordance with this invention, the inhibition of aldose reductase enzyme is observed with alkyl or alkenyl phenols of formula (I):

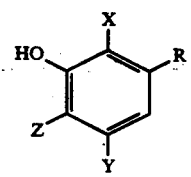

wherein R is alkyl having from 15 to 17 carbon atoms or alkenyl having from 15 to 17 carbon atoms; X is hydrogen or carboxyl; Y is hydrogen or hydroxyl; and Z is hydrogen or alkyl having from 1 to 4 carbon atoms.

Also useful in this invention are pharmaceutically acceptable base salts of the compounds of the formula (I).

This invention further provides a method of ameliorating chronic complications in a galactosemic or diabetic host, which comprises administering to the host an effective amount of a compound of the formula (I) or a pharmaceutically acceptable base salt thereof.

Additionally claimed is a method of inhibiting the action of aldose reductase in a galactosemic or diabetic host, which comprises administering to the host an aldose reductase inhibiting amount of a compound of the formula (I) or a pharmaceutically acceptable base salt thereof.

Also provided in this invention is a pharmaceutical composition comprising a pharmaceutically acceptable carrier and a compound of the formula (I) or a pharmaceutically acceptable salt thereof in an amount sufficient to ameliorate diabetes-associated complications.

DETAILED DESCRIPTION OF THE INVENTION

The compounds of the formula (I) are known and described in I. Kubo, et al., J. Argric. Food Chem. 34, 970–973 (1986). These compounds are found in certain plant species and can be isolated in quantities from cashew (*Anacardium occidentale*) nut shells. Kubo et al. reports the detailed isolation procedure, the disclosure of which is herein incorporated by reference. The utility of compounds of formula (I) wherein X is carboxyl, Y and Z are both hydrogen, and R is pentadecyl or 10(Z)-pentadecenyl as a prostaglandin synthetase inhibitor is also disclosed in I. Kubo, et al., Chem. Letters 1101, 1987. The anticancer activity of compounds of the formula (I) wherein X is carboxyl, Y and Z are both hydrogen, and R is $C_{15}$–$C_{17}$ alkyl or $C_{15}$–$C_{17}$ alkenyl disclosed in Japan Kokai No. 64-34,913 to Nishino, et al. Also, GB 1281,526 describes an anti-diabetic composition containing an aqueous or aqueous alcoholic extract of bark, root or leaves of *Anacardium occidentale.*

A preferred group of compounds of the formula (I), because of their greater effectiveness relative to other substitution, are those wherein X, Y and Z are each hydrogen.

A second preferred group of compounds of the formula (I) are those wherein X is carboxyl; and Y and Z are each hydrogen.

A third preferred group of compounds of the formula (I) are those wherein X is hydrogen; Y is hydroxyl; and Z is alkyl having from 1 to 4 carbon atoms. Within this preferred group, Z is more preferably methyl.

A fourth preferred group of compounds of the formula (I) are those wherein X and Z are each hydrogen; and Y is hydroxyl.

Within each preferred group, a particularly preferred subgroup of compounds are those wherein R is an alkyl of 15 carbon atoms or an alkenyl of 15 carbon atoms which may contain up to three double bonds in the alkenyl group. Especially preferred values for the R substituent in the formula (I) are 8(Z),11(Z),14-pentadecatrienyl; 8(Z),11(Z)-pentadecadienyl; 8(z)-pentadecenyl; and pentadecyl.

The pharmaceutically acceptable base salts of compounds of the formula (I) are those formed from bases which form non-toxic base salts. These particular non-toxic base salts include, but are not limited to; sodium, potassium, calcium, and magnesium. These salts can easily be prepared by treating the acidic compounds of the formula (I) with an aqueous solution of the desired cation, and then evaporating the resulting solution to dryness while preferably being placed under reduced pressure.

Alternatively, pharmaceutically acceptable base salts may also be prepared by mixing lower alkanolic solutions of the acidic compounds and the desired alkali metal alkoxide together, and then evaporating the resulting solution to dryness in the same manner as above. In either case, stoichiometric quantities of reagents are preferably employed in order to endure complete reaction and maximum yield of the desired pharmaceutically acceptable base salts.

In the treatment of diabetes-associated complications in a galactosemic or diabetic host, or in the inhibition of the action of aldose reductase in the same host, the compounds of formula (I) can be administered via the oral or parenteral routes. However, it is generally preferred to administer these compounds in their pharmaceutically acceptable base salts orally. In general, these compounds are most desirably administered in doses ranging from about 10 mg to about 1 g per day, although variations will still necessarily occur depending upon the weight of the host being treated. However, a dosage level that is in range of from about 1 mg to about 50 mg per kg of body weight per day is most desirably employed in order to achieve effective results, with a preferred oral range in human about 2.0-30.0 mg/kg. Other variations may also occur in this respect, depending upon the host being treated and the host's individual response to the medicament, as well as on the particular type of pharmaceutical formulation chosen and the time period and interval at which such administration is carried out. In some instances, dosage levels below the lower limit of the aforesaid range may be more than adequate, while in other cases still larger doses may be employed without causing any harmful or deleterious side effects to occur provided that such higher dose levels are first divided into several smaller doses that are to be administered throughout the day.

For purposes of oral administration, tablets containing various excipients such as sodium citrate, calcium carbonate and dicalcium phosphate may be employed along with various disintegrants such as starch and preferably potato or tapioca starch, alginic acid and certain complex silicates, together with binding agents such as polyvinylpyrrolidone, sucrose, gelatin and acacia. Additionally, lubricating agents such as magnesium stearate, sodium lauryl sulfate and talc are often very useful for tableting purposes. Solid compositions of a similar type may be employed as fillers in soft elastic and hard-filled gelatin capsules; preferred materials in this connection also include lactose or milk sugar as well as high molecular weight polyethylene glycols. When aqueous suspensions and/or elixirs are desired for oral administration, the essential active ingredient may be combined with various sweetening or flavoring agents, coloring matter or dyes and, if so desired, emulsifying and/or suspending agents, together with such diluents as water, ethanol, propylene glycol, glycerin and various like combinations thereof.

Although the preferred mode of administration of the compounds of the formula (I) or their pharmaceutically acceptable salts is oral, they may be administered parenterally as well.

For purposes of paternal administration, solutions of these particular compounds in sesame or peanut oil or in aqueous propylene glycol may be employed, as well as sterile aqueous solutions of the corresponding water-soluble base salts previously enumerated. Such aqueous solutions should be suitably buffered if necessary and the liquid diluent rendered isotonic with sufficient saline or glucose. These particular aqueous solutions are especially suitable for intravenous, intramuscular and subcutaneous injection purposes. In this connection, the sterile aqueous media employed are readily obtained by standard techniques well known to those skilled in the art. For instances, distilled water is ordinarily used as the liquid diluent and the final preparation is passed through a suitable bacterial filter, such as a sintered-glass filter, or a diatomaceous-earth or unglazed porcelain filter.

The activity of the compounds of the formula (I), as agents for the control of chronic diabetic complications, is determined by their ability to successfully pass one or more of the following standard biological or pharmacological tests, viz., (1) measuring their ability to inhibit the enzyme activity of isolated aldose reductase; (2) measuring their ability to reduce or inhibit sorbitol accumulation in the sciatic nerve of acutely streptozotocinized (i.e., diabetic) rats; (3) measuring their ability to reverse already-elevated sorbitol levels in the sciatic nerve and lens of chronic streptozotocin-induced diabetic rats; (4) measuring their ability to prevent or inhibit galactitol formation on the lens of acutely galactosemic rats; and (5) measuring their ability to delay cataract formation and reduce the severity of lens opacities in chronic galactosemic rats.

The method of this invention, and composition for accomplishing the method, can be conducted with the use of more than one compound of the formula (I) such as the mixture of several preferred compounds. However, in the following examples, only one particular compound was tested for its activity in each experiment.

The following examples are provided for the purpose of further illustration. Accordingly, it should be understood that the invention is not limited to the specific details of these examples.

Proton nuclear magnetic resonance spectra (NMR) were measured at 500 MHz for solutions in deuterochloroform (CDCl$_3$) and peaks are expressed in parts per million (ppm) downfield from tetramethylsilane. The peak shapes are denoted as follows: s, singlet; d, doublet; t, triplet; m, multiplet; b, broad.

PREPARATION 1

6-Pentadecylsalicylic Acid

The title compound was prepared according to the method of Kubo [I. Kubo, et al., Chem. Letters, 1101, 1987]. A sample of the product obtained had a melting point of 90°–91° C. and spectrascopic characteristics which are identical with those of the authentic sample.

PREPARATION 2

3-Pentadecylphenol

A mixture of unsaturated cardanols was isolated from cashew shell oil by following the procedure described in I. Kubo, et al., J. Agric. Food Chem., 34, 971 (1986). Catalytic hydrogenation of the mixture over Pd/C (5%) in methanol gave the title compound, which had the following spectroscopic characteristics: NMR (CDCl$_3$): 7.12 (t, 1H), 6.74 (d, 1H), 6.64 (s, 1H), 6.62 (m, 1H), 2.54 (m, 2H), 2.00 (bs, 2H), 1.2–1.3 (bs, 22H), 0.88 (t, 3H); ms m/e (relative intensity) 304 (M+, 12), 108 (C$_7$H$_7$O+H, 100).

PREPARATION 3

5-Pentadecylresorcinol

The title compound was prepared in a similar manner as described in Preparation 2 using a mixture of unsaturated cardols (isolated from cashew shell oil). The title compound had the following spectroscopic characteristics: NMR (CDCl$_3$): 6.22 (s, 2H), 6.14 (s, 1H), 4.62 (bs, 1H, OH), 2.46 (t, 2H), 1.53 (bs, 4H), 1.2–1.3 (bs, 22H) 0.86 (t, 3H); ms m/e (relative intensity) 320 (M+, 10), 124 (C$_7$H$_7$O$_2$+H, 100).

PREPARATION 4

2-Methyl-5-pentadecylresorcinol

The title compound was prepared in a similar manner as described in Preparation 2 using a mixture of unsaturated methylcardols (isolated from cashew shell oil). The title compound had the following spectroscopic characteristics: NMR (CDCl$_3$): 6.21 (s, 2H), 4.62 (s, 2H, OH), 2.42 (m, 2H), 1.53 (bs, 4H), 1.2–1.3 (bs, 22H), 0.84 (t, 3H); ms m/e (relative intensity) 334 (M+, 12), 138 (C$_8$H$_{10}$O$_2$, 100).

PREPARATIONS 5–16

The following compounds were isolated from cashew nut oil substantially according to the method of I. Kubo, et al., as described in J. Agric. Food Chem., 34, 970–973 (1986):

6-[8(z)-pentadecenyl]salicylic acid, 6-[8(z),11(z)-pentadecadienyl]salicylic acid, 6-[8(z),11(z),14-pentadecatrienyl]salicylic acid, 3-[8(z)-pentadecenyl]phenol, 3-[8(z),11(z)-pentadecadienyl]phenol, 3-[8(z),11(z),14-pentadecatrienyl]phenol, 2-methyl-5-[8(z)-pentadecenyl]resorcinol, 2-methyl-5-[8(z),11(z)-pentadecadienyl]resorcinol, 2-methyl-5-[8(z),11(z),14-pentadecatrienyl]resorcinol, 5-[8(z)-pentadecenyl]resorcinol, 5-[8(z),11(z)-pentadecadienyl]resorcinol, and 5-[8(z),11(z),14-pentadecatrienyl]resorcinol.

EXAMPLE 1

Aldose Reductase Inhibition

The following phenols were tested for their ability to inhibit aldose reductase enzyme activity.

| Compound | R | X | Y | Z |
| --- | --- | --- | --- | --- |
| 1 | Pentadecyl | COOH | H | H |
| 2 | 8(Z)-Pentadecenyl | COOH | H | H |
| 3 | 8(Z), 11(Z)-Pentadecadienyl | COOH | H | H |
| 4 | 8(Z), 11(Z), 14-Pentadecatrienyl | COOH | H | H |
| 5 | Pentadecanyl | H | H | H |
| 6 | 8(Z)-Pentadecenyl | H | H | H |
| 7 | 8(Z), 11(Z)-Pentadecadienyl | H | H | H |
| 8 | 8(Z), 11(Z), 14-Pentadecatrienyl | H | H | H |
| 9 | Pentadecyl | H | OH | CH$_3$ |
| 10 | 8(Z)-Pentadecenyl | H | OH | CH$_3$ |
| 11 | 8(Z), 11(Z)-Pentadecadienyl | H | OH | CH$_3$ |
| 12 | 8(Z), 11(Z), 14-Pentadecatrienyl | H | OH | CH$_3$ |
| 13 | Pentadecyl | H | OH | H |
| 14 | 8(Z)-Pentadecenyl | H | OH | H |
| 15 | 8(Z), 11(Z)-Pentadecadienyl | H | OH | H |
| 16 | 8(Z), 11(Z), 14-Pentadecatrienyl | H | OH | H |

The assay was conducted essentially according to the procedure of S. Hayman, et al., as described in the Journal of Biological Chemistry, 240, 877 (1965).

The preparation of aldose reductase was conducted according to the procedure of K. Inagaki et al., ARchives of Biochemistry and Biophysics, 216, 337 (1982). Briefly, lenses were removed from calf eyes and homogenized. The enzyme was isolated from the homogenized preparation by successive chromatography on a DEAE-sephacel column (Pharmacia LKB Biotechnology, Piscataway, N.J.), an affinity column (Matrex gel red A; Amicon Co., Danvers, Mass.), and a Sephadex G-75 column (Pharmacia LKB Biotechnology, Piscataway, N.J.).

A reaction mixture of 0.1M sodium phosphate buffer (pH 6.2), 0.4M ammonium sulfate, 10 mm glyceraldehyde, 0.16 mm NADPH, and 10 ml propylene glycol solution containing the purified enzyme was prepared. The test compound was incubated with the enzyme in the reaction mixture.

Aldose reductase activity was assayed spectrophotometrically by determining the decrease in the NADPH concentration at 340 nm in a Beckman DU-64 spectrophotometer (Beckman, Palo Alto, Calif.).

The percent inhibition of each compound was calculated by comparing the reaction rate of the solution containing substrate and the compound at a given concentration with that of the control solution containing only substrate.

The results obtained with each compound are expressed below in terms of percent inhibition of enzyme activity with respect to the various concentration levels tested.

TABLE 1

| Compound | Percent Inhibition (%) | | | | |
|---|---|---|---|---|---|
| | $10^{-5}M$ (× 2.9) | $10^{-5}M$ (× 1.5) | $10^{-6}M$ (× 7.5) | $10^{-6}M$ (× 3.8) | $10^{-6}M$ (× 1.9) |
| 1 | | 66 | 40 | 27 | |
| 2 | | | 91 | 42 | 9 |
| 3 | | | 91 | 18 | 1 |
| 4 | | | 77 | 60 | 47 |
| 5 | 11 | | | | |
| 6 | 10 | | | | |
| 7 | 44 | | | | |
| 8 | 72 | 45 | 38 | | |
| 10 | 53 | | | | |
| 11 | | 56 | 43 | 22 | |
| 12 | | 65 | 53 | 28 | |
| 13 | 52 | | | | |
| 14 | | | 87 | 58 | 9 |
| 15 | | | 86 | 57 | 7 |
| 16 | | | 85 | 16 | 12 |

These data in Table 1 show that the compounds tested significantly inhibit the aldose reductase activity at low concentrations and that potent inhibition is particularly observed with those in which X is carboxyl, and Y and Z are both hydrogen (anacardic acids), as well as those in which X and Z are both hydrogen and Y is hydroxyl.

EXAMPLE 2

A dry solid pharmaceutical composition is prepared by blending the following materials together in the proportions by weight specified below:

| | |
|---|---|
| 6-[8(Z),11(Z),14-Pentadecatrienyl] salicylic acid | 50 |
| Sodium citrate | 25 |
| Alginic acid | 10 |
| Polyvinylpyrrolidone | 10 |
| Magnesium stearate | 5 |

After the dried composition is thoroughly blended, tablets are punched from the resulting mixture, each tablet being of such size that it contains 200 mg of the active ingredient. Other tablets are also prepared in a similar fashion containing 25, 50 and 100 mg of the active ingredient, respectively, by merely using the appropriate amount of the salicylic acid compound in each case.

EXAMPLE 3

A dry solid pharmaceutical composition is prepared by combining the following materials together in the proportions by weight indicated:

| | |
|---|---|
| 6-[8(Z),11(Z),14-Pentadecatrienyl] salicylic acid | 50 |
| Calcium carbonate | 20 |
| Polyethylene glycol, average molecular weight 4000 | 30 |

The dried solid mixture so prepared is then thoroughly agitated so as to obtain a powdered product that is completely uniform in every respect. Soft elastic and hard-filled gelatin capsules containing this pharmaceutical composition are then prepared, employing a sufficient quantity of material in each instance so as to provide each capsule with 250 mg of the active ingredient.

The invention now being fully described, it will be apparent to one of ordinary skill in the art many changes and modifications can be made without departing from the spirit or scope of the invention.

I claim:

1. A method of inhibiting the action of aldose reductase enzyme in a diabetic host in need of treatment of diabetic conditions, which comprises administering to the host an aldose reductase enzyme inhibiting amount of a compound having the formula:

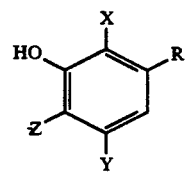

or a pharmaceutically acceptable salt thereof, wherein R is alkyl having from 15 to 17 carbon atoms or alkenyl having from 15 to 17 carbon atoms; X is hydrogen or carboxyl; Y is hydrogen or hydroxyl; and Z is hydrogen or alkyl having from one to four carbon atoms.

2. The method according to claim 1, wherein the diabetic conditions are diabetic neuropathy.

* * * * *